United States Patent

Nishiyama et al.

[11] 4,321,388
[45] Mar. 23, 1982

[54] N-BENZOYL N'-PYRIDYLOXY PHENYL UREA

[75] Inventors: Ryuzo Nishiyama, Takatsuki; Hiroyuki Mori; Yasuo Ogawa, both of Moriyama; Takahiro Haga; Kuniaki Nagatani, both of Kusatsu, all of Japan

[73] Assignee: Ishihara Sangyo Kaisha Ltd., Osaka, Japan

[21] Appl. No.: 183,281

[22] Filed: Sep. 2, 1980

[30] Foreign Application Priority Data

Sep. 11, 1979 [JP] Japan .................. 54-116359

[51] Int. Cl.³ ............................................ C07D 213/64
[52] U.S. Cl. .................................. 546/291; 424/263
[58] Field of Search ............................ 546/291

[56] References Cited

U.S. PATENT DOCUMENTS 3,748,356  7/1973  Wellinga et al. .................. 564/44
4,005,223  1/1977  Sirrenberg et al. ................ 424/322
4,173,637  11/1979  Nishiyama et al. ................ 546/300
4,173,638  11/1979  Nishiyama et al. ................ 546/300

Primary Examiner—Alan L. Rotman
Attorney, Agent, or Firm—Oblon, Fisher, Spivak, McClelland & Maier

[57] ABSTRACT

Compounds having the formula

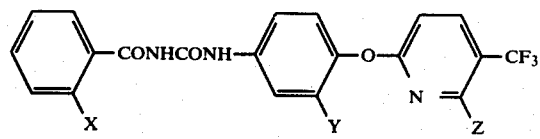

wherein X represents a halogen atom, nitro, methyl, or trifluoromethyl group; Y represents a halogen or hydrogen atom or methyl group; and Z represents a halogen atom are useful as agricultural chemicals and pharmaceuticals.

6 Claims, No Drawings

N-BENZOYL N'-PYRIDYLOXY PHENYL UREA

BACKGROUND OF THE INVENTION

1. Field of the Invention

The present invention relates to novel N-benzoyl N'-pyridyloxy phenyl ureas and the process for producing the same.

2. Description of the Prior Arts

N-benzoyl N'-phenyl ureas are disclosed in U.S. Pat. No. 3,748,356 and N-benzoyl N'-phenoxy phenyl ureas (no pyridyloxy group) are disclosed in U.S. Pat. No. 4,005,223. The inventors have also disclosed certain N-benzoyl N'-pyridyloxy phenyl ureas in U.S. Pat. No. 4,173,638 and U.S. Pat. No. 4,173,637.

The inventors have further studied to find other kinds of N-benzoyl N'-pyridyloxy phenyl ureas in view of resistivities and special effects and low toxicities.

SUMMARY OF THE INVENTION

It is an object of the present invention to provide novel N-benzoyl N'-pyridyloxy phenyl ureas.

It is another object of the present invention to provide a process for producing N-benzoyl N'-pyridyloxy phenyl ureas.

The novel compounds of the present invention are N-benzoyl N'-pyridyloxy phenyl ureas having the formula

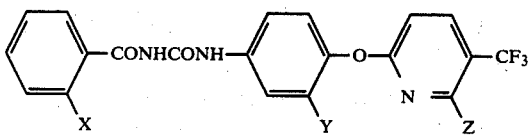

(I)

wherein X represents a halogen atom, nitro, methyl, or trifluoromethyl group; Y represents a halogen or hydrogen atom or methyl group; and Z represents a halogen atom.

The novel compounds of the present invention are useful as agricultural chemicals and pharmaceuticals with low toxicity.

DETAILED DESCRIPTION OF THE PREFERRED EMBODIMENTS

The novel compounds of the present invention, N-benzoyl N'-pyridyloxy phenyl ureas having the formula (I)

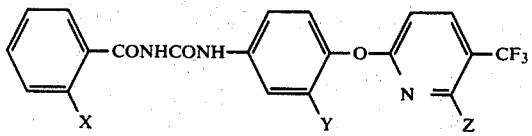

wherein X represents a halogen atom, nitro, methyl, or trifluoromethyl group; Y represents a halogen or hydrogen atom or methyl group; and Z represents a halogen atom are produced by reacting a compound having the formula

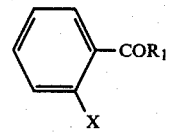

(II)

wherein X is defined above and $R_1$ represents amino or isocyanate group with a compound having the formula

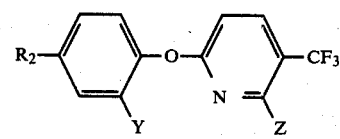

(III)

wherein Y and Z are defined above and $R_2$ represents amino or isocyanate group; and $R_2$ is isocyanate group in the case that $R_1$ is amino group and $R_2$ is amino group in the case that $R_1$ is isocyanate group.

The reaction is preferably carried out in the presence of a solvent. Suitable solvents include benzene, toluene, xylene, pyridine, monochlorobenzene, ethyl acetate, dioxane, dimethylsulfoxide, tetrahydrofuran etc.

N-benzoyl N'-pyridyloxy phenyl ureas having the formula (I) are usually produced by the process (A) or (B).

Process (A)

The object compound is produced by reacting a compound having the formula

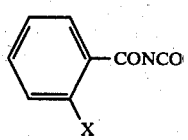

(IV)

wherein X is defined above; with a pyridyloxy aniline compound having the formula

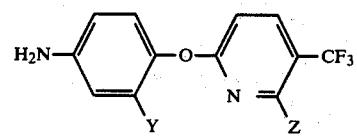

(V)

wherein Y and Z are defined above; in said solvent at 0° to 120° C. for 0.1 to 24 hours.

Process (B)

The object compound is produced by reacting a compound having the formula

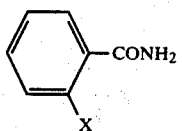

(VI)

wherein X is defined above; with a pyridyloxy phenyl isocyanate compound having the formula

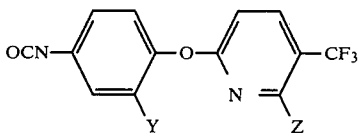
(VII)

wherein Y and Z are defined above; at 50° C. to a refluxing temperature for 0.1 to 24 hours.

The pyridyloxy aniline compounds having the formula (V) can be produced by reacting a compound having the formula

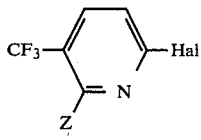

with a compound having the formula

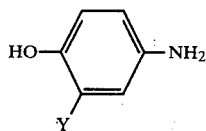

in a solvent in the presence of a base at 70° to 150° C. for 0.5 to 10 hours.

Suitable bases include sodium hydroxide, potassium hydroxide, sodium carbonate and potassium carbonate. Suitable solvents include aprotonic polar solvents such as dimethylsulfoxide, dimethylformamide and hexamethylphosphoroamide, and ketones such as acetone, methylethyl ketone and methylisobutyl ketone.

The pyridyloxy phenylisocyanate compound having the formula (VII) can be produced by reacting a compound having the formula

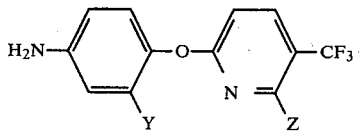
(VIII)

wherein Y and Z are defined above; with phosgene having the formula

COCl$_2$ at 50° to 150° C. for 0.1 to 24 hours in a solvent.

Suitable solvents are inert to phosgene and include toluene, xylene, monochlorobenzene, ethyl acetate and dioxane.

Certain examples of preparation of the compounds of the present invention will be described.

EXAMPLE 1

In a flask, a solution of 1.43 g. of 2-chloro-4-aminophenol in 20 ml. of dimethylsulfoxide and 1.12 g. of potassium hydroxide were charged and the mixture was heated at 140° C. for 1 hour to produce a potassium salt. The reaction mixture was cooled to the ambient temperature. A solution of 2.16 g. of 2,6-dichloro-3-trifluoromethyl pyridine in 10 ml. of dimethylsulfoxide was added dropwise during 10 minutes. The mixture was heated at 100° C. for 2 hours to react them. After the reaction, the reaction mixture was poured into water and extracted with methylene chloride. The extracted product was washed with water and dehydrated over anhydrous sodium sulfate. Methylenechloride was distilled off to obtain 2.16 g. of 3-chloro-4-(5-trifluoromethyl-6-chloro-2-pyridyloxy)aniline (melting point of 76° to 78° C.).

In a flask, a solution of 3.2 g. of 3-chloro-4-(5-trifluoromethyl-6-chloro-2-pyridyloxy)aniline in 40 ml. of dioxane was charged and then, a solution of 1.8 g. of 2-chlorobenzoylisocyanate in 20 ml. of dioxane was added dropwise during 10 minutes with stirring, and the reaction was continued at the ambient temperature for 5 hours. After the reaction, the reaction product was poured into water. The precipitate was separated by a filtration and washed with a cold methanol and dried to obtain 4.6 g. of N-2-chlorobenzoyl-N'-[3-chloro-4-(5-trifluoromethyl-6-chloro-2-pyridyloxy)phenyl] urea having a melting point of 194° to 196° C.

EXAMPLE 2

In a flask, 20 ml. of dioxane and 3.2 g. of 3-chloro-4-(5-trifluoromethyl-6-chloro-2-pyridyloxy)aniline were charged to dissolve the latter. A solution of 1.9 g. of 2-nitrobenzoylisocyanate in 10 ml. of dioxane was added dropwise with stirring at for 15 minutes to the former solution to react them at the ambient temperature for 6 hours. After the reaction, the reaction mixture was poured into water. The precipitate was separated by a filtration and washed with methanol to obtain 4.8 g. of N-(2-nitrobenzoyl)N'-[3-chloro-4-(5-trifluoromethyl-6-chloro-2-pyridyloxy)phenyl]urea having a melting point of 187° to 190° C.

EXAMPLE 3

In a flask, 75 ml. of toluene was charged and dried phosgene gas was fed to saturate it. A solution of 9 g. of 3-chloro-4-(5-trifluoromethyl-6-chloro-2-pyridyloxy)aniline in 75 ml. of toluene was added dropwise to the former solution at 80° C. under feeding phosgene to be excess in the system. After the addition, phosgene was fed for 5 to 10 minutes and excess of phosgene was distilled off by raising the temperature to stoichiometrically obtain 3-chloro-4-(5-trifluoromethyl-6-chloro-2-pyridyloxy)phenylisocyanate. A solution of 2-bromobenzamide in 30 ml. of toluene was added to the product and the mixture was refluxed at 110° C. for 20 hours. The reaction mixture was poured into 200 ml. of water and the product was extracted with 100 ml. of ethyl acetate. The organic layer was dehydrated over anhydrous sodium sulfate and the solvent was distilled off. The product was washed with a small amount of toluene to obtain 10.5 g. of N-(2-bromobenzoyl)N'-3-chloro-4-(5-trifluoromethyl-6-chloro-2-pyridyloxy)phenyl urea having a melting point of 168° to 171° C.

The following compounds were produced by the same process.

Compound No. 1: N-2-chlorobenzoyl N'-[3-chloro-4-(5-trifluoromethyl-6-chloro-2-pyridyloxy)phenyl-]urea; m.p.: 194°–196° C.

Compound No. 2: N-(2-fluorobenzoyl)N'-[3-chloro-4-(5-trifluoromethyl-6-chloro-2-pyridyloxy)phenyl-]urea; m.p.: 207°–210° C.

Compound No. 3: N-(2-bromobenzoyl)N'-[3-chloro-4-(5-trifluoromethyl-6-chloro2-pyridyloxy)phenyl]urea; m.p.: 168°–171° C.

Compound No. 4: N-(2-nitrobenzoyl)N'-[3-chloro-4-(5-trifluoromethyl-6-chloro-2-pyridyloxy)phenyl]urea: m.p.: 187°–190° C.

Compound No. 5: N-(2-trifluoromethylbenzoyl)N'-[3-chloro-4-(5-trifluoromethyl-6-chloro-2-pyridyloxy)-phenyl]urea; m.p.: 171°–174° C.

Compound No. 6: N-(b 2-methylbenzoyl)N'-[3-chloro-4-(5-trifluoromethyl-6-chloro-2-pyridyloxy)phenyl]urea; m.p.: 192°–195° C.

Compound No. 7: N-(2-chlorobenzoyl)N'-[3-fluoro-4-(5-trifluoromethyl-6-chloro-2-pyridyloxy)phenyl]urea; m.p.: 185°–191° C.

Compound No. 8: N-(2-chlorobenzoyl)N'-[3-bromo-4-(5-trifluoromethyl-6-chloro-2-pyridyloxy)phenyl]urea; m.p.: 172°–175° C.

Compound No. 9: N-(2-chlorobenzoyl)N'-[3-methyl-4-(5-trifluoromethyl-6-chloro-2-pyridyloxy)phenyl]urea; m.p.: 157°–160° C.

Compound No. 10: N-(2-chlorobenzoyl)N'-[3-chloro-4-(5-trifluoromethyl-6-bromo-2-pyridyloxy)phenyl]urea; m.p.: 177°–180° C.

Compound No. 11: N-(2-chlorobenzoyl)N'-[3-chloro-4-(5-trifluoromethyl-6-fluoro-2-pyridyloxy)phenyl]urea; m.p.: 180°–182° C.

Compound No. 12: N-(2-chlorobenzoyl)N'-[4-(5-trifluoromethyl-6-chloro-2-pyridyloxy)phenyl]urea; m.p.: 156°–157° C.

The compounds of the present invention have excellent effects as pharmaceuticals such as antitumors and agricultural chemicals such as insecticides.

When the compounds of the present invention are used as antitumors, suitable formulations and administrations can be selected as the conventional ones. For example, the compound of the present invention is mixed with a diluent to prepare a desired formulation such as a powder, a tablet, a capsule or an injection. In usual, those compounds are administered at a dose of 10–500 mg/kg/day.

When the compounds of the present invention are used as agricultural chemicals, suitable formulations can be selected as the conventional agricultural chemicals. The compound of the present invention can be formulated with various adjuvants, to form an emulsifiable concentrate, a dust, a wettable powder and a solution.

The insecticide is applied in a concentration of 1 to 10,000 ppm preferably 20 to 2,000 ppm of the active ingredient.

Test 1

Antitumor bioassay was performed by using each compound of the present invention. The results of the tests for therapeutic effects to P-388 mouse leukemia of the compounds are shown in Table 1.

The tests were performed by the method described in Cancer Chemotherapy Reports, Part 3, Vol. 3, No. 2 September 1972, page 2.

During 1st to 3rd days or 1st to 5th days for 3 days or 5 days or only 1st and 5th days for 2 days after intraperitoneal transplantation of P-388 mouse leukemia to CDF mice, the compound of the present invention was intraperitoneally administered at a dose defined in Table 1.

The life prolong effect was calculated by the following equation:

TABLE 1

$$\text{Life prolong effect (T/C)} = \frac{\text{Median survival time of treated group}}{\text{Median survival time of control group}} \times 100\ (\%)$$

| Active ingredient | Compound 1 | | | | | | 5-FU | | Control |
|---|---|---|---|---|---|---|---|---|---|
| Dose (mg/kg/day) | 200 | 100 | 50 | 25 | 200 | 100 | 20 | — |
| Aministration day after transplantation | 1 to 3 | 1 to 5 | 1 to 5 | 1 to 5 | 1 and 5 | 1 and 5 | 1 to 5 | — |
| Total dose (mg/kg) | 600 | 500 | 250 | 125 | 400 | 200 | 100 | — |
| Median survival time (days) | 21.5 | 19.5 | 18.5 | 12.8 | 18.5 | 13.0 | 21.5 | 10.5 |
| Life prolong effect (T/C) (%) | 205 | 186 | 176 | 122 | 176 | 124 | 205 | 100 |

Note: 5-FU: 5-fluorouracil

Test 2

In accordance with the method of Test 1 except administering each of the compounds shown in Table 2 after 1st day and 4th days from the transplantation of P-388 mouse leukemia, each test was carried out. The results are shown in Table 2.

TABLE 2

| Active ingredient | Comp. 2 | Comp. 3 | Comp. 4 | Comp. 5 | Comp. 6 | Comp. 12 | 5-FU |
|---|---|---|---|---|---|---|---|
| Dose (mg/kg/day) | 400 | 400 | 400 | 400 | 400 | 400 | 60 |
| Administration day after transplantation | 1st and 4th day | 1st and 4th day | 1st and 4th day | 1st and 4th day | 1st and 4th day | 1st and 4th day | 1st and 4th day |
| Total dose (mg/kg) | 800 | 800 | 800 | 800 | 800 | 800 | 120 |
| Life prolong effect (%) | 134 | 176 | 200 | 125 | 140 | 187 | 185 |

Test 3

Each compound of the present invention was dissolved in 1000 μg/ml. of acetone and diluted with water for 10 times. Into 1 ml. of Yoshida Sarcoma cells cultured medium, (Yoshida Sarcoma cell: 4 to $8 \times 10^4$/ml.), 10 μl of the diluted medium was added dropwise to culture at 37° C. for 48 hours. Condition of growth of Yoshida Sarcoma cells was observed. The results are shown in Table 3 wherein the reference + means to control the growth of Yoshida Sarcoma cells to less than 50% of that of non-treatment.

TABLE 3

| Active ingredient | Result | Active ingredient | Result |
|---|---|---|---|
| Comp. 2 | + | Comp. 7 | + |
| 3 | + | 8 | + |
| 4 | + | 10 | + |
| 5 | + | 11 | + |

TABLE 3-continued

| Active ingredient | Result | Active ingredient | Result |
| --- | --- | --- | --- |
| 6 | + | 12 | + |

Test 4

The active ingredients were respectively dispersed in water to prepare dispersions having a concentration of 400 ppm. Leaves of cabbage were dipped into the dispersions for about 10 seconds and taken out and dried under passing air.

A piece of moistened filter paper was put on each Petri dish (diameter 9 cm) and the dried leaves of cabbage were put on the filter paper and larvae of tobacco cutwarm in 2nd or 3rd instar were fed on them and the Petri dishes were covered and kept in constant temperature at 28° C. with lightening. After 6 days from the treatment with the dispersion, the mortal larvae were measured and the mortality rates were calculated by the following equation:

TABLE 4

$$\text{Mortality rate} = \frac{\text{mortal larvae}}{\text{total larvae}} \times 100$$

| Active ingredient | Mortality rate |
| --- | --- |
| Comp. 1 | 90 |
| 2 | 100 |
| 3 | 100 |
| 4 | 90 |
| 6 | 100 |
| 8 | 100 |
| 9 | 100 |
| 10 | 100 |

Test 5

In each Petri dish (diameter 9 cm), about 250 ml. of a solution of each compound of the present invention at a concentration of 100 ppb was charged and mosquitos (*Culex pipens molestus*) in 3rd instar were fed on it. The Petri dishes were covered and kept in constant temperature at 28° C. with lightening. After 10 days, the mortal larvae were measured and the mortality rates were calculated by the equation of Test 4. The results are shown in Table 5.

TABLE 5

| Active ingredient | Mortality rate |
| --- | --- |
| Comp. 1 | 80 |
| 2 | 100 |
| 3 | 100 |
| 4 | 90 |
| 5 | 80 |
| 6 | 100 |
| 7 | 100 |
| 8 | 100 |
| 9 | 100 |
| 10 | 100 |

We claim:

1. N-benzoyl N'-pyridyloxy phenyl urea having the formula

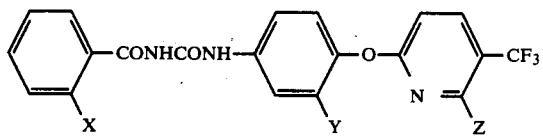

wherein X represents a halogen atom, nitro, methyl, or trifluoromethyl group; Y represents a halogen or hydrogen atom group; and Z represents a halogen atom.

2. N-benzoyl N'-pyridyloxy phenyl urea having the formula

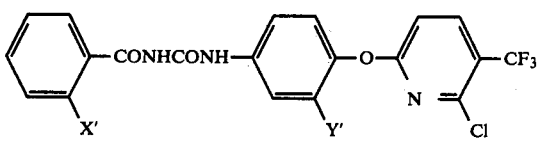

wherein X' represents a halogen atom or nitro group; and Y' represents hydrogen or chlorine atom.

3. N-2-chlorobenzoyl N'-[3-chloro-4-(5-trifluoromethyl-6-chloro-2-pyridyloxy) phenyl] urea.

4. N-2-bromobenzoyl N'-[3-chloro-4-(5-trifluoromethyl-6-chloro-2-pyridyloxy) phenyl] urea.

5. N-2-nitrobenzoyl N'-[3-chloro-4-(5-trifluoromethyl-6-chloro-2-pyridyloxy) phenyl] urea.

6. N-2-chlorobenzoyl N'-[4-[5-trifluoromethyl-6-chloro-2-pyridyloxy) phenyl] urea.

* * * * *